United States Patent [19]

Nakagawa et al.

[11] 4,022,776
[45] May 10, 1977

[54] 5-[1-HYDROXY-2-(SUBSTITUTED-AMINO)]ETHYL-8-HYDROXY-CARBOSTYRIL DERIVATIVES

[75] Inventors: Kazuyuki Nakagawa, Tokushima; Shiro Yoshizaki, Naruto; Kaoru Tanimura; Shigeharu Tamada, both of Tokushima, all of Japan

[73] Assignee: Otsuka Pharmaceutical Company Limited, Tokyo, Japan

[22] Filed: Dec. 26, 1974

[21] Appl. No.: 536,705

[30] Foreign Application Priority Data

| Jan. 31, 1974 | Japan | 49-12953 |
|---|---|---|
| Jan. 31, 1974 | Japan | 49-12954 |
| Feb. 5, 1974 | Japan | 49-15116 |
| Feb. 7, 1974 | Japan | 49-15953 |
| Feb. 5, 1974 | Japan | 49-15115 |
| Feb. 18, 1974 | Japan | 49-19787 |
| Feb. 27, 1974 | Japan | 49-23604 |
| Nov. 11, 1974 | Japan | 49-130717 |
| Nov. 11, 1974 | Japan | 49-130718 |
| Nov. 11, 1974 | Japan | 49-130719 |
| Nov. 11, 1974 | Japan | 49-130725 |
| Nov. 11, 1974 | Japan | 49-130727 |
| Dec. 4, 1974 | Japan | 49-140339 |
| Dec. 4, 1974 | Japan | 49-140340 |

[52] U.S. Cl. .................. 260/247.2 A; 424/248.54; 424/250; 424/258; 260/247.5 GP; 260/268 BQ; 260/287 R; 260/288 R; 260/288 CE; 260/289 K
[51] Int. Cl.² .............. C07D 215/26; C07D 413/06
[58] Field of Search ............... 260/247.2, 288, 268, 260/247.2 A, 288 R, 288 CE, 268 BQ

[56] References Cited

UNITED STATES PATENTS

| 2,770,619 | 11/1956 | Schraufstatter et al. | 260/288 R |
|---|---|---|---|
| 3,444,173 | 5/1969 | Goldman | 260/247.5 GP |
| 3,644,353 | 2/1972 | Lunts et al. | 260/559 S |

OTHER PUBLICATIONS

Snyder, Organic Synthetics, vol. 28, p. 26–27, (1948).

*Primary Examiner*—Henry R. Jiles
*Assistant Examiner*—R. W. Ramsuer
*Attorney, Agent, or Firm*—Sughrue, Rothwell, Mion, Zinn & Macpeak

[57] ABSTRACT

5-[Hydroxy-2-(substituted-amino)]ethyl-8-hydroxy-carbostyril derivatives represented by the formula (I)

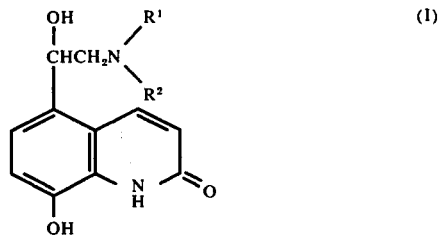

wherein $R^1$ and $R^2$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^1$ and $R^2$ may, when taken together with the nitrogen atom to which they are attached, form a 5 or 6-membered substituted or unsubstituted heterocyclic ring containing 1 or 2 nitrogen, oxygen or sulfur atoms as hetero atoms, the pharmaceutically acceptable acid addition salts thereof and a process for preparing the above compounds.

11 Claims, No Drawings

5-[1-HYDROXY-2-(SUBSTITUTED-AMINO)]ETHYL-8-HYDROXYCARBOSTYRIL DERIVATIVES

BACKGROUND OF THE INVENTION

1. Field of the Invention

This invention relates to novel carbostyril derivatives and a process for preparing the same. More particularly, this invention relates to novel 5-[1-hydroxy-2-(substituted -amino)]-ethyl-8-hydroxycarbostyril derivatives and a process for preparing the same.

2. Description of the Prior Art

It is well known that certain carbostyril derivatives exhibit useful pharmaceutical activities. Representative compounds of this type have been disclosed in *Journal of Medical Chemistry*, Vol. 15, No. 3, pp260–266 (1972), Japanese Patent Publication No. 38789/1971 and *Chemical Abstracts*, 62, 16212e (1965), etc. However, these prior art references do not teach that the compounds having a 1-hydroxy-2-(substituted-amino)-ethyl group at the 5-position of the carbostyril moiety possess an excellent β-adreno-receptor stimulating activity.

It has now been found that 8-hydroxy-carbostyril derivatives having a 1-hydroxy-2-(substituted-amino)ethyl group at the 5-position of the carbostyril moiety and the pharmaceutically acceptable acid addition salts thereof possess a β-adreno-receptor stimulating activity, and therefore, are useful as a therapeutic agent such as a bronchodilator, a peripheral vasodilator and an antihypertensive agent, particularly for treating bronchial asthma.

SUMMARY OF THE INVENTION

The present invention provides novel 5-[1-hydroxy-2-(substituted-amino)]ethyl-8-hydroxycarbostyril derivatives having

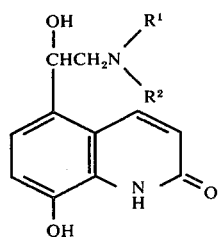
(I)

wherein $R^1$ and $R^2$, which may be the same or different, each represents a hydrogen atom or an alkyl group having 1 to 4 carbon atoms, an aralkyl group containing a straight or branched chain alkyl moiety having 1 to 4 carbon atoms or a cycloalkyl group having 4 to 6 carbon atoms, or $R^1$ and $R^2$ may, when taken together with the nitrogen atom to which they are attached, form a 5 or 6-membered substituted or unsubstituted heterocyclic ring containing 1 or 2 nitrogen, oxygen or sulfur atoms as hetero atoms.

This invention also provides a process for preparing the above 5-[1-hydroxy-2-(substituted-amino) ]ethyl-8-hydroxycarbostyril derivatives represented by the formula (I)

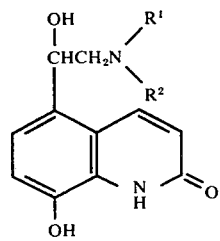
(I)

wherein $R^1$ and $R^2$, which may be the same or different, each represents a hydrogen atom or an alkyl group having 1 to 4 carbon atoms, an aralkyl group containing a straight or branched chain alkyl moiety having 1 to 4 carbon atoms or a cycloalkyl group having 4 to 6 carbon atoms, or $R^1$ and $R^2$ may, when taken together with the nitrogen atom to which they are attached, form a 5 or 6-membered substituted or unsubstituted heterocyclic ring containing 1 or 2 nitrogen, oxygen or sulfur atoms as hetero atoms, which comprises the steps of 1. reacting 8-hydroxycarbostyril represented by the formula (VII)

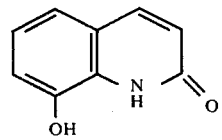
(VII)

and a haloacetyl halide in the presence or absence of a solvent and in the presence of a Lewis acid catalyst to prepare a 5-haloacetyl-8-hydroxycarbostyril derivative represented by the formula (IV)

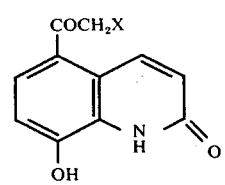
(IV)

wherein X represents a halogen atom, 2. reacting the resulting 5-haloacetyl-8-hydroxycarbostyril derivative represented by the formula (IV) and an amine represented by the formula (III)

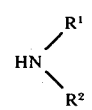
(III)

wherein $R^1$ and $R^2$ are as defined above in the presence or absence of a solvent to prepare a 5-substituted-aminoacetyl-8-hydroxycarbostyril derivative represented by the formula (II)

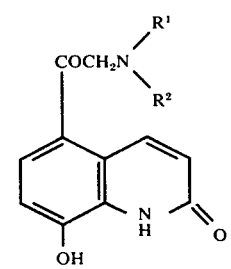
(II)

wherein R¹ and R² are as defined above; and 3. reducing the resulting 5-substituted-aminoacetyl-8-hydroxycarbostyril derivative represented by the formula (II) with hydrogen in the presence of a catalyst or with a reducing agent.

DETAILED DESCRIPTION OF THE INVENTION

The 5-[1-hydroxy-2-(substituted-amino)]ethyl-8-hydroxycarbostyril derivatives of the formula (I) and the salts thereof are novel compounds and exhibit a $\beta$-adreno-receptor stimulating activity and, therefore, are useful as a bronchodilator, a peripheral vasodilator or an antihypertensive agent, particularly for treating bronchial asthma.

The term "alkyl" as used herein means a straight or branched chain alkyl group having 1 to 4 carbon atoms, and includes, for example, a methyl, ethyl, propyl, iso-propyl, butyl, sec-butyl, tert-butyl group and the like.

The term "aralkyl" as used herein means an aralkyl group containing a straight or branched chain alkyl moiety having 1 to 4 carbon atoms, for example, a benzyl, α-methylbenzyl, α,α-dimethylbenzyl, phenethyl, α,α-dimethylphenethyl group and a like group.

The term "cycloalkyl" as used herein means a cycloalkyl group having 4 to 6 carbon atoms, for example, a cyclopentyl, cyclobutyl, cyclohexyl group and the like.

The term "5- or 6-memberd substituted or unsubstituted heterocyclic ring" used herein means heterocyclic groups containing 1 or 2 nitrogen, oxygen or sulfur atoms as hetero atoms such as a pyrrolidino, pyrrolidinyl, piperidino, piperidinyl, morpholino, morpholinyl, piperazino, piperazinyl or a like group which can be unsubstituted or substituted with an alkyl group having 1 to 4 carbon atoms, such as a methyl, ethyl, iso-propyl, tert-butyl group and the like, for example, a 2-methylpiperidino, 3-methylpiperidino, N-methylpiperazino group and the like.

The term "halogen" used herein means fluorine, chlorine, bromine and iodine, preferably chlorine and bromine.

The compounds of the present invention represented by the formula (I) can be prepared from an 8-hydroxycarbostyril according to the following reaction scheme:

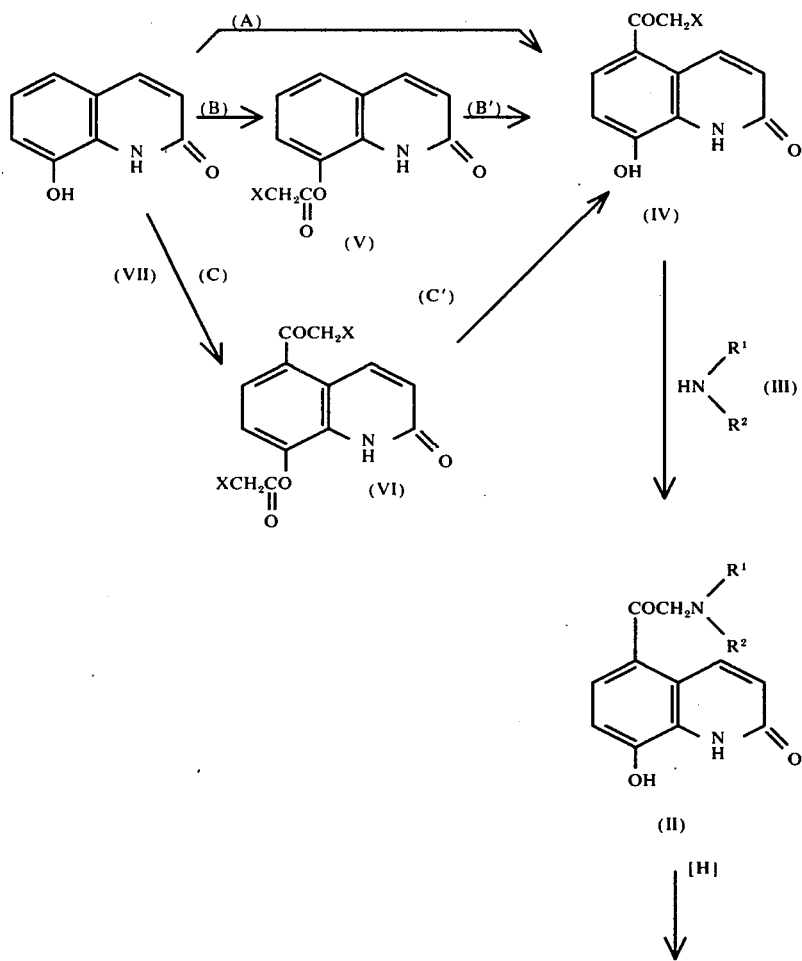

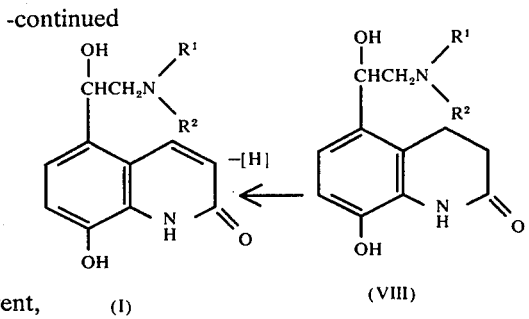

wherein $R^1$ and $R^2$, which may be the same or different, each represents a hydrogen atom or an alkyl group having 1 to 4 carbon atoms, an aralkyl group containing a straight or branched chain alkyl moiety having 1 to 4 carbon atoms or a cycloalkyl group having 4 to 6 carbon atoms, or $R^1$ and $R^2$ may, when taken together with the nitrogen atom to which they are attached, form a 5or 6-membered substituted or unsubstituted heterocyclic ring containing 1 or 2 nitrogen, oxygen or sulfur atoms as hetero atoms and X represents a halogen atom such as a chlorine, bromine, iodine or fluorine atom.

The 8-hydroxycarbostyril of the formula (VII) used as a starting material in the preparation of the compounds of the formula (IV) is a known compound and can easily be prepared by, for example, the method as disclosed in George R. Pettit et al., J. Org. Chem., 33, 1089 (1968).

As illustrated in the above reaction scheme, the 5-haloacetyl-8-hydroxycarbostyril represented by the formula (IV) which is an intermediate in the process of this invention can be prepared by one of the alternative routes (A), (B)+(B') or (C)+(C').

In the route (A), an 8hydroxycarbostyril of the formula (VII) is reacted with a haloacetyl halide in the presence or absence of a solvent and in the presence of a well-known Lewis acid catalyst to form the 5-haloacetyl-8-hydroxycarbonstyril intermediate of the formula (IV) in one step.

In the route (B)+(B'), the reaction between the starting material (VII) and the haloacetyl halide results in the production of a novel 8-haloacetoxycarbostyril of the formula (V)

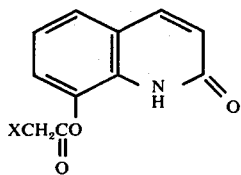

(V)

wherein X is a halogen atom, which is then subjected to the rearrangement of the haloacetyl group to form the intermediate of the formula (IV).

In the route (C)+(C'), the reaction between the starting material (VII) and the haloacetyl halide results in the production of a novel 5-haloacetyl-8-haloacetoxycarbonstyril of the formula (VI)

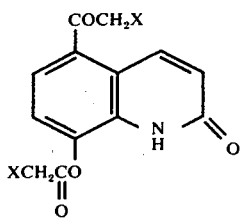

(VI)

X is as defined above, which is then subjected to hydrolysis to remove the 8-haloacetyl group to form the intermediate (IV).

In practice, the reaction between the 8-hydroxycarbostyril and the haloacetyl halide proceeds via a combination of the above described three reaction routes, i.e., (A), (B)+(B') and (C)+(C'). Therefore, the reaction product is obtained as a mixture of the compounds of the formulae (IV), (V) and (VI). Generally, when the reaction is conducted at relatively low temperatures, the resulting product would be a mixture of the compounds of the formulae (IV) and (V) with a small amount of the compound of the formula (VI), whereas if the reaction is conducted at relatively high temperatures, the resulting product would be a mixture of the compounds of the formulae (IV) and (VI) with a small amount of the compound of the formula (V).

Isolation of the compound of the formulae (IV), (V) or (VI) from the reaction product can be advantageously carried out by well known procedures, for example, by fractional crystallization.

In a preferred embodiment, after completion of the reaction, the solvent used is removed by distillation to obtain a residue or the reaction mixture is poured into crushed ice to precipitate crystals. The residue or the crystals are washed with hot water or cool methanol. The insoluble substances are recrystallized from methanol to obtain the 5-haloacetyl-8-hydroxycarbostyril of the formula (IV). The residual methanolic mother liquor is concentrated to dryness under reduced pressure, and the residue is recrystalized from acetone to obtain the 8-haloacetoxycarbostyril of the formula (V). The resulting acetone mother liquor is then concentrated to dryness under reduced pressure, and the residue is recrystallized from acetone or ethyl acetate to obtain the 5-haloacetyl-8-haloacetoxycarbostyril of the formula (VI).

The thus obtained 5-haloacetyl-8-hydroxycarbostyril intermediate of the formula (IV) is then reacted with a secondary or tertiary organic amine represented by the formula (III)

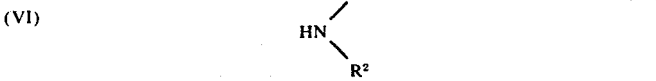

wherein $R^1$ and $R^2$ are as defined above, in the presence or absence of a solvent to obtain a novel 5-substituted-aminoacetyl-8-hydroxycarbostyril derivative represented by the formula (II)

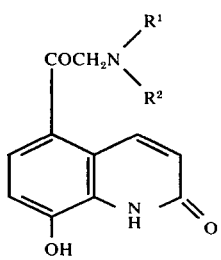

(II)

wherein R[1] and R[2] are as defined above.

The 5-[1-hydroxy-2-(substituted-amino)]ethyl-8-hydroxycarbostyril derivative of the formula (I) of the present invention can be prepared by reducing the above obtained 5-substituted-aminoacetyl-8-hydroxycarbostyril derivative of the formula (II).

Both the 5-substituted-aminoacetyl-8-hydroxycarbostyril derivatives of the formula (II), an intermediate product of the present invention, and the final product, 5-[1-hydroxy-2-(substituted-amino)]-ethyl-8-hydroxycarbostyril derivatives of the formula (I) are novel compounds.

The process according to the present invention will be hereinafter illustrated in greater detail.

The haloacetyl halide which is used in the present invention as a reactant in the preparation of the compound of the formula (IV) includes those having a chlorine, bromine, iodine or fluorine atom as the halogen atom, with chloroacetyl chloride being preferred.

In the reaction route (A), the catalyst which can be used is a usual Lewis acid, for example, aluminum chloride or bromide, zinc chloride, ferric chloride, stannic chloride, titanium chloride, boron trifluoride and the like with aluminum chloride being preferably used. The catalyst is used in an amount of from about 2 to about 10 moles, preferably 3 to 6 moles, per mole of the 8-hydroxycarbostyril.

This reaction can be effected in the absence of a solvent but the reaction proceeds more smoothly in an inert organic solvent. Suitable examples of inert organic solvents which can be used in this reaction are carbon disulfide, nitrobenzene, diethyl ether, dioxane and the like, preferably, carbon disulfide. These inert organic solvents are usually used in a volume of about 0.5 to about 20, preferably 2 to 10, times the volume of the reactants. The reaction can be advantageously carried out under anhydrous condition.

Reaction (A) is generally conducted using an equimolar amount to a large excess of the haloacetyl halide, preferably about 2 to about 20 moles, most preferably 2 to 10 moles, of the haloacetyl halide per mole of the 8-hydroxycarbostyril of the formula (VII). The reaction proceeds at room temperature (about 20° to 30° C) to about 150° C, preferably room temperature to 80° C. The reaction time varies depending upon the reaction temperature employed, but is usually from about 1 to 20 hours, preferably 1 to 10 hours.

Reaction (B) can be carried out using the same amount of the same catalyst as used in reaction (A) in the same solvent as used in reaction (A) or in the absence of a solvent. This reaction can be carried out using an equimolar amount to a large excess of the haloacetyl halide, preferably from about 2 to about 20 moles, most preferably 2 to 10 moles, per mole of the 8-hydroxycarbostyril of the formula (VII) at a temperature of from room temperature to about 150° C, preferably from room temperature to 80° C, for about 1 to about 20 hours, preferably 1 to 10 hours.

Reaction (B') to obtain a 5-haloacetyl-8-hydroxycarbostyril of the formula (IV) from the 8-haloacetoxycarbostyril of the formula (V) obtained in reaction (B) as above described is generally known as a Fries rearrangement, and can be carried out using the same amount of the same catalyst as in reaction (A) in the same solvent as in reaction (A) or in the absence of any solvent. The reaction temperature ranges from room temperature to about 150° C, preferably room temperature to 80° C and the reaction time ranges from about 1 to 20, preferably 1 to 10, hours. This reaction can proceed in the presence of any haloacetyl halide which remains unreacted in the previous reaction system (B). In such a case, it was found that the presence of the haloacetyl halide improves the yield of the product, the 5-haloacetyl-8-hydroxycarbostyril of the formula (IV).

Reaction (C) can be carried out using the same amount of the same catalyst as used in reaction (A) in the same solvent as used in reaction (A) or in the absence of any solvent. The haloacetyl halide is used in an equimolar amount to a large excess, but preferably in an amount of about 2 to about 20 moles, preferably 2 to 10 moles, per mole of the 8-hydroxycarbostyril of the formula (VII). The reaction temperature is from about room temperature to about 150° C, preferably room temperature to 80° C, and the reaction time is from about 1 to about 20 hours, preferably 1 to 10 hours.

Reaction (C') to obtain the compound of the formula (IV) from the above obtained 5-haloacetyl-8-haloacetoxycarbostyril can be conducted using a catalyst, for example, a basic substance such as an alkali metal hydroxide or carbonate, e.g., sodium hydroxide, potassium hydroxide, sodium carbonate, potassium carbonate and the like or an inorganic acid, e.g., hydrochloric acid, sulfuric acid, phosphoric acid and the like in the presence of a solvent, for example, water, a lower alcohol such as ethanol, methanol, isopropanol and the like. The amount of the catalyst varies depending upon the type of catalyst used. For example, hydrochloric acid or sodium hydroxide and the like is used in an amount of from about 1 to about 5 moles per mole of the 5-haloacetyl-8-haloacetoxycarbostyril of the formula (VI). The reaction generally proceeds at a temperature of about 0° to about 150° C for about 0.5 to about 5 hours, but it is advantageous to carry out the reaction at a temperature of from 0° to 40° C when a basic substance is used as a catalyst and at a temperature of 70° to 100° C when an inorganic acid is used as a catalyst.

The amines of the formula (III) which can be used as a reactant in the preparation of the 5-substituted-aminoacetyl-8-hydroxycarbostyril derivative of the formula (II) include alkylamines, for example, methylamine, ethylamine, n-propylamine, iso-propylamine, n-butylamine, sec-butylamine, tert-butylamine and the like; cycloalkylamines, for example, cyclobutylamine, cyclopentylamine, cyclohexylamine; aralkylamines, for example, benzylamine, α-methylbenzylamine, α,α-dimethylbenzylamine, phenethylamine, α,α-dimethylphenethylamine and the like; and substituted or unsubstituted heterocyclic amines, for example, pyrrolidine, piperidine, morpholine, piperazine, 2-methylpiperidine, 3-methylpiperidine, N-methylpiperazine and the like.

The reaction between the 5-haloacetyl-8-hydroxycarbostyril intermediate of the formula (IV) and the amine of the formula (III) can be carried out in the absence of a solvent since the amine reactant itself also serves as a solvent but it is advantageous to conduct this reaction in an appropriate solvent. Suitable examples of solvents which can be used in this reaction include lower alcohols such as methanol, ethanol, isopropanol and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferred.

This reaction can be effected using an equimolar amount to, especially in the absence of a solvent, a large excess of the amine of the formula (III), preferably from about 2 to about 10 moles of the amine per mole of 5-haloacetyl-8-hydroxycarbostyril of the formula (IV) at room temperature to a refluxing temperature of the reaction system, preferably 40° to 100° C at about atmospheric pressure to about 10 atmospheres.

The reduction of the above obtained 5-substituted-aminoacetyl-8-hydroxycarbostyril derivative of the formula (II) to a 5-[1-hydroxy-2-(substituted-amino)-]ethyl-8-hydroxycarbostryil derivative of the formula (I) can be conducted by a conventional reduction using a reducing agent such as lithium aluminum hydride, sodium borohydride and the like or a conventional catalytic reduction in the presence of a catalyst such as palladium black, platinum oxide, palladium-on-carbon, Raney nickel, platinum black and the like and hydrogen. The above reducing agent can be used in an amount of from about 2 to about 10 moles, preferably 2 to 5 moles, per mole of the carbostyril compound of the formula (II) in a solvent while cooling, under atmospheric pressure at a temperature of about 0° to 100° C, preferably 20° to 50° C. When sodium borohydride is used as a reducing agent, the solvent is preferably water or alcohols such as methanol, ethanol, propanols, and the like, etc., and when lithium aluminum hydride is used as a reducing agent, the solvent is preferably a non-aqueous solvent such as anhydrous diethyl ether, ethyl acetate, tetrahydrofuran and the like.

The catalytic reduction can be carried out using the above catalyst in an amount of from about 0.05 to about 1, preferably 0.1 to 0.5, per mole of carbostyril compound of the formula (II) in a solvent, for example, water or an alcohol such as methanol, ethanol or isopropanol at a temperature of from room temperature to about 150° C, preferably room temperature to 120° C, advantageously with agitating the reduction system under a hydrogen atmosphere at a pressure of from atmospheric pressure to about 100 atmospheres, preferably from atmospheric pressure to 50 atmospheres. It is advantageous to carry out the above catalytic reduction at a temperature higher than about 50° C at atmospheric pressure or at a temperature higher than room temperature under pressure.

The compounds of the present invention represented by the formula (I) wherein $R^1$ and $R^2$ represent hydrogen atoms can also be prepared from the compounds of the formula (II) wherein either $R^1$ or $R^2$ represents a benzyl group or an α-methylbenzyl group. The above benzyl or α-methylbenzyl group can easily be split off during the catalytic reduction to produce the compounds of the present invention wherein $R^1$ and $R^2$ are hydrogen atoms.

The compounds of the present invention represented by the formula (I) can also be prepared by dehydrogenating the corresponding 3,4-dihydrocarbostyril derivatives of the formula (VIII)

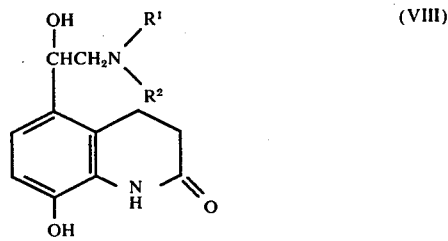

wherein $R^1$ and $R^2$ are as described above, which are disclosed in co-pending U.S. Patent Application Ser. No. 536,704 filed Dec. 26, 1974 filed simultaneously herewith.

The dehydrogenation can be conducted by any known procedure which is capable of releasing a hydrogen atom from each of the 3- and 4-positions of the carbostyril moiety to form a double bond between the 3- and 4-positions. This dehydrogenation can be attained by (1) a procedure using a dehydrogenating agent, for example, chloranil (tetrachloro-1,4-benzoquinone), dichlorodicyano-1,4-benzoquinone and the like; (2) a procedure using a dehydrogenating metal catalyst such as palladium black, platinum black, platinum oxide, Raney nickel and the like; or (3) a procedure using a dehydrogenating agent such as sulfur, selenium dioxide and the like, advantageously using the above procedure (1) or (2). Either of the dehydrogenation can be carried out in a solvent such as aromatic hydrocarbons, for example, benzene, toluene, xylene, phenetol, chlorobenzene and the like; lower alcohols, for example, methanol, ethanol, isopropanol, tertbutanol and the like, ethers, for example, dioxane; ketones, for example, acetone and the like; water; acetic acid; etc. The dehydrogenation can advantageously be carried out at a temperature of from room temperature to the refluxing temperature of the dehydrogenation system, preferably at or near the refluxing temperature for a period of from about 10 to about 30 hours. THe dehydrogenation agent is generally used in an amount of about 1 to about 5 moles per mole of the 3,4-dihydrocarbostyril of the formula (VIII), and the metal catalyst is generally used in an amount of about 0.5 to about 3 moles per mole of the 3,4-dihydrocarbostyril of the formula (VIII).

Both the compounds of the formula (II) and the compounds of the formula (I) as obtained above are basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc. or organic acids such as oxalic acid, maleic acid, fumaric acid, malic acid, tartaric acid, citric acid, ascorbic acid, etc. These acid addition salts can easily be prepared by the well-known procedures, for example, by adding an equimolar to an excess amount of the acid to a solution of the compound dissolved in an appropriate organic solvent such as methanol, ethanol, iso-propanol, acetone and the like.

Both the free bases of the compounds of the formula (I) and the acid addition salts thereof exhibit a stimulating activity on β-adreno-receptor and, therefore, are very useful as pharmaceuticals for treating disorders such as bronchial asthma.

Particularly preferred compounds of the formula (I) are the following basic compounds and their hydrochlorides, sulfates, phosphates, maleates, fumarates and oxalates.

5-(1-Hydroxy-2-isopropylamino)ethyl-8-hydroxycarbostyril 5-(1-Hydroxy-2-sec-butylamino)ethyl-8-hydroxycarbostyril 5-(1-Hydroxy-2-tert-butylamino)ethyl-8-hydroxycarbostyril 5-[1-Hydroxy-2-(α-methylbenzylamino)]ethyl-8-hydroxycarbostyril 5-[1-Hydroxy-2-(α,α-dimethylphenethylamino)]ethyl-8-hydroxycarbostyril 5-(1-Hydroxy-2-piperidino)ethyl-8-hydroxycarbostyril 5-(1-Hydroxy-2-morpholino)ethyl-8-hydroxycarbostyril 5-(1-Hydroxy-2-benzylamino)ethyl-8-hydroxycarbostyril 5-[1-Hydroxy-2-(1-phenethylamino)]ethyl-8-hydroxycarbostyril 5-(1-Hydroxy-2-amino)ethyl-8-hydroxycarbostyril.

As is apparent to one skilled in the art, the compounds of the present invention contain two asymmetrical centers and, therefore, can be present in four optically active forms.

The present invention is further illustrated in greater detail by reference to the following Examples, but these examples are given for illustrative purposes only and are not to be construed as limiting the scope of the invention. Unless otherwise indicated, all parts, percents, ratios and the like are by weight.

EXAMPLE 1

27 g of 8-hydroxycarbostyril (VII) and 37 ml of chloroacetyl chloride were dissolved in 250 ml of nitrobenzene, and to the resulting solution was added 85 g of aluminum chloride followed by stirring at 70° C for 20 hours. 500 ml of 10% aqueous hydrochloric acid was added to the reaction mixture and the nitrobenzene was removed by steam distillation. After cooling the mixture, the precipitated crystals were collected by filtration which were then washed with 300 ml of hot water. Recrystallization from methanol gave 14.0 g of 5-chloroacetyl-8-hydroxycarbostyril (IV) having a melting point of 285°–287° C (with decomposition) as pale yellow crystals.

EXAMPLE 2

20 g of aluminum chloride was added to 5.0 g of 8-hydroxycarbostyril (VII) and the resulting mixture was thoroughly mixed. 10 g of chloroacetyl chloride was gradually added to the mixture while ice-cooling. The mixture was allowed to react by heating at 40° to 45° C for 2 hours to form 8-chloroacetoxycarbostyril (V) followed by stirring at 70° C for 3 hours. After cooling, the precipitated crystals were collected by filtration, and the crystals were washed with 300 ml of water followed by recrystallization from methanol to obtain 2.6 g of 5-chloroacetyl-8-hydroxycarbostyril (IV) having a melting point of 285°–287° C (with decomposition) as pale yellow crystals.

On the other hand, a part of the 8-chloroacetoxycarbostyril (V) which had been formed in this example was removed and recrystallized from acetone to give pale yellow crystals. The melting point of these crystals was found to be 248°–250° C (with decomposition).

EXAMPLE 3

1.5 g of chloroacetyl chloride and 20 ml of carbon disulfide were added to 0.5 g of 8-hydroxycarbostyril (VII), and 2 g of aluminum chloride was gradually added to the resulting solution while ice-cooling. After thorough stirring, the mixture was gradually heated and refluxed for 30 minutes. After cooling, the unreacted chloroacetyl chloride and the carbon disulfide were removed, and crushed ice was added to the resulting residue to crystallize the product. The crystals thus obtained were washed with water and then recrystallized from acetone to obtain 0.45 g of 8-chloroacetoxycarbostyril(V) having a melting point of 248°–251° C (with decomposition) as pale yellow crystals.

EXAMPLE 4

20 g of aluminum chloride and 10 g of chloroacetyl chloride were added to 10 g of the 8-chloroacetoxycarbostyril (V) obtained in Example 3, and the resulting mixture was heated at 75° to 85° C for 1 hour. The mixture was poured onto crushed ice while warm and the precipitated crystals were filtered, washed with water and recrystallized from methanol to obtain 3.7 g of 5-chloroacetyl-8-hydroxycarbostyril(IV) having a melting point of 285°–287° C (with decomposition) as pale yellow crystals.

EXAMPLE 5

7.3 g of 8-hydroxycarbostyril(VII) and 12.5 g of chloroacetyl chloride were added to 70 ml of nitrobenzene, and 30 g of aluminum chloride was gradually added to the resulting solution while stirring under ice-cooling. The mixture was stirred at 50° to 55° C for 6 hours followed by pouring into ice-water. The precipitated crystals were filtered, washed with methanol and recrystallized from acetone to obtain 3.5 g of 5-chloroacetyl-8-chloroacetoxycarbostyril (VI) having a melting point of 239°–241° C (with decomposition) as pale yellow crystals.

EXAMPLE 6

1.7 g of the 5-chloroadetyl-8-chloroacetoxycarbostyril (VI) obtained in Example 5 was added to 50 ml of 10% aqueous hydrochloric acid followed by stirring at 95° to 100° C for 2 hours. After cooling, the precipitated crystals were filtered, washed with water and then recrystallized from methanol to obtain 1.1 g of 5-chloroacetyl-8-hydroxycarbostyril (IV) having a melting point of 285°–286° C (with decomposition) as pale yellow crystals.

EXAMPLE 7

2.5 g of the 5-chloroacetyl-8-chloroacetoxycarbostyril (VI) obtained in Example 5 was added to 30 ml of 5% aqueous potassium hydroxide followed by stirring at 20° to 25° C for 30 minutes. The resulting solution was adjusted to a pH of 2 to 3 with diluted hydrochloric acid while cooling. The precipitated crystals were filtered, washed with water and recrystallized from methanol to obtain 1.7 g of 5-chloroacetyl-8-hydroxycarbostril (IV) having a melting point of 285°–287° C (with decomposition) as pale yellow crystals.

EXAMPLE 8

20 g of aluminum chloride was gradually added to a mixture of 4.5 g of 8-hydroxycarbostyril, and 10 g of chloroacetyl cloride while stirring under ice-cooling. The resulting mixture was stirred at 55° to 60° C for 8 hours to form 5-chloroacetyl-8-chloroacetoxycarbostyril. 40 ml of 5% potassium hydroxide was then added to the reaction mixture followed by stirring at room temperature for 30 minutes. A 10% aqueous hydrochloric acid solution was added thereto to make the solution acidic to form crystals. The precipitated crystals were filtered, washed with water and then recrystallized from methanol to obtain 2.3 g of 5-chloroacetyl-8-hydroxycarbostyril (IV) having a melting point of 285°–286° C (with decomp.) as pale yellow crystals.

On the other hand, a part of the above reaction mixture before the addition of the 5% aqueous potassium hydroxide as described above was taken out and poured into ice-water. The precipitated crystals were filtered, washed with methanol and recrystallized from ethyl acetate to obtain 5-chloroacetyl-8-chloroacetoxycarbostyril (VI) having a melting point of 238°–241° C (decomposition) as pale yellow crystals.

EXAMPLE 9

12.6 g of the 5-chloroacetyl-8-hydroxycarbostyril (IV) obtained in Example 4 or 8 was suspended in 130 ml of isopropanol, and 2515 g of isopropylamine (III) was added dropwise to the resulting suspension while stirring. The reaction mixture was then stirred at 55° to 60° C for 3 hours. After cooling, concentrated hydrochloric acid was added to the mixture to adjust the mixture to a pH of 2 to 3, and the precipitated crystals were filtered, washed with acetone and recrystallized from methanol-dimethylformamide (1:1 by volume) to obtain 6.5 g of 5-isopropylainoacetyl-8-hydroxycarbostyril (II) hydrochloride having a melting point of 286° – 288° C (with decomposition as pale yellow crystals.

EXAMPLE 10

8.0 g of the 5-chloroacetyl-8-hydroxycarbostyril (IV) (IV) obtained Example 4 or 8 was suspended in 100 ml of ethanol, and 10 g of tert-butylamine was added dropwise to the resulting suspension while stirring followed by strring at 55° to 60° C for 5 hours. After the mixture was concentrated to half the volume, concentrated hydrochloric acid was added thereto to adjust the mixture to a pH of 2 to 3. The precipitated crystals were filtered, washed with acetone and recrystallized from ethanol to obtain 4.1 g of 5-tert-butylaminoacetyl-8-hydroxycarbostyril (II) having a melting point of 291° – 293° C (with decomposition) as pale yellow crystals.

EXAMPLE 11

4.3 g of the 5-chloroacetyl-8-hydroxycarbostyril (IV) obtained in Example 4 or 8 was suspended in 50 ml of ethanol, and 5 g of sec-butylamine was added dropwise to the resulting suspension while stirring followed by stirring at 60° to 65° C for 5 hours. After cooling, the resulting mixture was adjusted to a pH of 3 with concentrated hydrochloric acid. The precipitated crystals were filtered, washed with acetone and recrystallized from methanol-ethanol (1:1 by volume) to obtain 2.9 g of 5-sec-butylaminoacetyl-8-hydroxycarbostyril (II) hydrochloride having a melting point of 289° – 291° C (with decomposition) as pale yellow crystals.

EXAMPLE 12

10 g of 5-chloroacetyl-8-hydroxycarbostyril (IV) prepared in Example 4 or 8 was suspended in 50 ml of benzene, and 10 ml of piperidine (III) was added to the suspension followed by allowing the mixture to react while heating under refluxing and stirring for 6 hours. The reaction mixture was filtered to recover the reaction product which was then washed with benzene and then with 50 ml of isopropanol. The resulting insoluble material was dissolved in 150 ml of a 2% aqueous hydrochloric acid. The solution was concentrated to dryness under reduced pressure and the resulting residue was recrystallized from ethanol to obtain 7.5 g of white amorphous 5-piperidinoacetyl-8-hydroxycarbostyril (II) hydrochloride ½ hydrate having a melting point of 239° – 241° C (with decomposition).

EXAMPLE 13

10 g of 5-chloroacetyl-8-hydroxycarbostyril (IV) prepared in Example 4 or 8 was suspended in 60 ml of benzene, and 9 ml of morpholine was added to the suspension followed by allowing the mixture to react while heating under refluxing and stirring for 4 hours. The reaction mixture was cooled and the resulting precipitate was filtered. The precipitate was dissolved in 60 ml of isopropanol and the solution was adjusted to a pH of 2 – 3 with concentrated hydrochloric acid. The resulting acidic solution was cooled with ice and the precipitate formed was filtered followed by recrystallization from ethanol. The precipitate was dissolved in 20 ml of water and the solution was adjusted to a pH 7.5 – 8.0 with sodium bicarbonate and ice-cooled. The precipitate formed upon cooling was filtered and recrystallized from ethanol to obtain 4.2 g of white amorphous 5-morpholinoacetyl-8-hydroxycarbostyril (II) having a melting point of 238° – 239.5° C (with decomposition). The product thus obtained was confirmed by IR and NMR spectral analyses and elemental analysis.

EXAMPLE 14

120 ml of benzylamine was added to 15 g of 5-chloroacetyl-8-hydroxycarbostyril (IV) prepared as described in Example 4 or 8, and the mixture was stirred for one hour at room temperature. The precipitate which as formed upon addition of petroleum ether to the reaction mixture was dissolved by addition of dilute hydrochloric acid and the solution was filtered to remove any remaining insoluble material. The hydrochloric acid layer was then concentrated to dryness, and the residue was recrystallized from methaol to obtain 16.4 g of a material having a melting point of 274° – 279° C (with coloring and decomposition). The product thus obtained was confirmed by NMR and IR spectral analyses and elemental analysis as 5-benzylaminoacetyl-8-hydroxycarbostyril (II) hydrochloride monohydrate.

EXAMPLE 15

10 g of 5-chloroacetyl-8-hydroxycarbostyril (IV) was dissolved in 50 ml of ethanol, and the 25 g of 1-phenethylamine (III) was added dropwise to the solution followed by stirring at a temperature of 50° C for 4 hours. The ethanol was then distilled off, and the precipitate was washed with diethyl ether and dissolved in isopropanol to remove any insoluble material. The isopropanol layer was concentrated to a volume of about 1/3 the original volume and adjusted to a pH of 4 with concentrated hydrochloric acid. The precipitate formed was recrystallized from a mixture of ethanol and acetone to obtain 9.8 g of a material having a melting point of 246° – 249° C. The product thus obtained was confirmed by NMR and IR spectral analysis and elemental analysis as 5-(1-phenethylaminoacetyl)-8-hydroxycarbostyril (II) hydrochloride.

EXAMPLE 16

40 ml of 1,1-dimethylphenethylamine (III) was added to 5 g of 5-chloroacetyl-8-hydroxycarbostyril (IV), and the mixture was stirred at room temperature in the dark for 5 hours. The precipitate which was formed upon addition of petroleum ether to the reaction mixture was washed with diethyl ether and dissolved in a methanolic solution of hydrochloric acid to remove any insoluble material. The methanol was then distilled off, and the residue was recrystallized from methanol to obtain 6.1 g of a material having a melting point of 246° – 247° C (with coloring and decomposition). The product thus obtained was confirmed by NMR and IR spectral analyses as 5-(1,1-dimethylphenethylaminoacetyl)-8-hydroxycarbostyril (II) hydrochloride 1/2 hydrate.

EXAMPLE 17

1.0 g of the 5-isopropylaminoacetyl-8-hydroxycarbostyril (II) hydrochloride obtained as described in Example 9 was dissolved in 40 ml of water, and 0.5 g of palladium-on-carbon was added to the resulting solution as a catalyst. The resulting mixture was heated to 35° to 40° C while stirring to absorb the hydrogen. Upon completion of the reduction reaction, the catalyst was filtered, and the filtrate was concentrated to dryness under reduced pressure. Ethanol was added to the residue and then repeatedly concentrated to dryness to completely remove the water. The residue was crystallized from acetone and recrystallized from ethanol-acetone (1:1 by volume) to obtain 0.4 g of pale yellow amorphous 5-(1-hydroxy-2-isopropylamino)ethyl-8hydroxycarbostyril (I) hydrochloride having a melting point of 210° – 212° C (with decomposition).

EXAMPLE 18

2.0 g of the free base of the 5-sec-butylaminoacetyl-8-hydroxycarbostyril (II) obtained as described in Example 11 was dissolved in 100 methanol, and 0.8 g of sodium borohydride was gradually added to the resulting solution while stirring under cooling. The resulting mixture was stirred at that temperature for 15 minutes followed by further stirring at room temperature for another 1 hour. Concentrated hydrochloric acid was added to the mixture to adjust the mixture to a pH of 1.5 to 2, and the solvent was removed by distillation under reduced pressure. To the residue was added 30 ml of ethanol, and then the mixture was concentrated to dryness under reduced pressure to remove water. The residue was dissolved in 50 ml of absolute ethanol, and an ethanolic solution of sodium hydroxide was added to the resulting solution to adjust the solution to a pH of 7 to 8.5. The precipitates thus formed were filtered, and the filtrate was concentrated to dryness under reduced pressure. The residue was then extracted with 50 ml of absolute ethanol, and hydrogen chloride was bubbled through the extract. The extract was concentrated to dryness under reduced pressure, and the residue was recrystallized from isopropyl alcohol to obtain 1.3 g of pale yellow amorphous 5-(1-hydroxy-2-sec-butylamino)ethyl-8-hydroxycarbostyril (I) dihydrochloride monohydrate having a melting point of 143° – 144° C (with decomposition).

EXAMPLE 19

1.5 g of the 5-tert-butylaminoacetyl-8-hydroxycarbostyril (II) obtained as described in Example 10 was dissolved in 100 ml of methanol, and 0.7 g of sodium borohydride was slowly added to the resulting solution while stirring under cooling. The stirring was further continued at that temperature for 15 minutes and at room temperature for an additional hour. The reaction product was worked up in the same manner as described in Example 18 and then recrystallized from ethanol to obtain 0.9 g of pale yellow amorphous 5-(1-hydroxy-2-tert-butylamino)-ethyl-8-hydroxycarbostyril (II) hydrochloride having a melting point of 242° – 244° C (with decomposition).

EXAMPLE 20

2.0 g of 5-piperidinoacetyl-8-hydroxycarbostyril (II) hydrochloride prepared as described in Example 12 was dissolved in 200 ml of methanol, and 2.0 g of sodium borohydride was added to the solution while ice-cooling followed by stirring the mixture for 2 hours. The mixture was adjusted to a pH of 2 to 3 with concentrated hydrochloric acid, and the mixture was allowed to stand for one hour at room temperature followed by filtration. The filtered reaction mixture was concentrated under reduced pressure, and residue was dissolved in 30 ml of ethanol. The solution was filtered to remove any insoluble material, and the filtrate was concentrated under reduced pressure. These procedures (dissolution in ethanol, filtration and concentration) were repeated three times. The resulting residue was dissolved in acetone by heating and the precipitate formed upon cooling was filtered and recrystallized from isopropanol to obtain 0.6 g of white amorphous 5-(1-hydroxy-2-piperidino)ethyl-8-hydroxycarbostyril (I) hydrochloride 1½ hydrate having a melting point of 146° – 148° C (with decomposition). The product thus obtained was confirmed by IR and NMR spectral analyses and elemental analysis.

EXAMPLE 21

1.0 g of 5-morpholinoacetyl-8-hydroxycarbostyril (II) prepared as in Example 13 was dissolved in 100 ml of methanol, and 1.2 g of sodium borohydride was added to the solution followed by allowing the mixture to react for 2 hours while stirring. The reaction mixture was adjusted to a pH of 2 – 3 with concentrated hydrochloric acid and the mixture was allowed to stand at room temperature for one hour. The reaction mixture was then filtered and the filtrate was concentrated under reduced pressure. The residue was dissolved in 20 ml of ethanol and the solution was filtered to remove any insoluble material followed by concentration of the filtrate under reduced pressure. These procedures (dissolution in ethanol, filtration and concentration) were repeated three times, and the residue thus obtained was crystallized from acetone. The precipitated crystals were filtered and triturated with 20 ml of an aqueous sodium bicarbonate solution to remove any soluble material by filtration, and the insoluble material was washed with water and dissolved in ethanol by heating. The resulting solution was adjusted to a pH of 2 – 3 with concentrated hydrochloric acid, and the precipitate formed upon cooling was filtered to obtain 0.6 g of white amorphous 5-(1-hydroxy-2-morpholino)ethyl-8-hydroxycarbostyril (I) hydrochloride 1½ hydrate having a melting point of 157° – 158.5° C (with decomposition). The product thus obtained was confirmed by IR and NMR spectral analyses and elemental analysis.

EXAMPLE 22

50 ml of methanol was added to 5 g of the free base of the 5-benzylaminoacetyl-8-hydroxycarbostyril (II) prepared as in Example 14, and 3 g of sodium borohydride was added slowly to the solution under ice-cooling and stirring followed by stirring the mixture at room temperature for one hour. The resulting mixture was adjusted to a pH of 1 with concentrated hydrochloric acid and the precipitate formed was filtered. The filtrate was concentrated to dryness and crystallized from acetone. The resulting crystals were adjusted to a pH 8 with an aqueous sodium hydroxide solution, the precipitate formed was filtered and washed with water. The precipitate was adjusted to a pH of 1 with dilute hydrochloric acid and concentrated to dryness. The residue thus obtained was recrystallized from a mixture of methanol and acetone to obtain 4.2 g of a white amorphous material having a melting point of 120° – 121° C. The product thus obtained was confirmed by NMR and IR spectral analyses and elemental analysis as 5-(1-hydroxy-2-benzylamino)ethyl-8hydroxycarbostyril (I) hydrochloride dihydrate.

EXAMPLE 23

1 g of the 5-(1-phenethylaminoacetyl)-8-hydroxycarbostyril (II) hydrochloride prepared as described in Example 15 was dissolved in 50 ml of methanol, and the solution was rendered weakly alkaline with a methanolic solution of sodium hydroxide. 0.5 g of sodium borohydride was then added slowly to the mixture while ice-cooling followed by stirring the mixture at room temperature for one hour. The precipitate which as formed upon addition of concentrated hydrochloric acid to a pH of 3 was filtered, and the filtrate was concentrated to dryness. The resulting residue was dissolved in absolute ethanol and the solution was adjusted to a pH of 9 with an ethanolic solution of sodium hydroxide. The precipitate was filtered, and the filtrate was concentrated to dryness. The residue was crystallized from acetone and washed with water. The resulting crystals were dissolved in isopropanol and the solution was saturated with hydrogen chloride gas followed by cooling. The precipitate formed was filtered and recrystallized from isopropanol to obtain 0.77 g of a white amorphous material having a melting point of 162° – 164° C. The product thus obtained was confirmed by NMR and IR spectral analyses and elemental analysis as 5-[1-hydroxy-2-(1-phenethylamino)]ethyl-8-hydroxycarbostyril (I) hydrochloride dihydrate.

EXAMPLE 24

0.1 g of platinum oxide and 50 ml of water were added to 0.5 g of the 5-benzylaminoacetyl-8-hydroxycarbostyril (II) hydrochloride monohydrate prepared as described in Example 14, and the mixture was reduced at room temperature under atmospheric pressure in a hydrogen atmosphere for 24 hours while shaking. After completion of the reduction, the catalyst was filtered and the aqueous phase was concentrated to dryness. The residue was recrystallized from a mixture of methanol and acetone to obtain 0.25 g of a white amorphous 5-(1-hydroxy-2-amino)ethyl-8-hydroxycarbostyril (I) hydrochloride having a melting point of 261° – 262° C (with decomposition). The product thus obtained was confirmed by IR and NMR spectral analyses and elemental analysis.

EXAMPLE 25

1.5 g of 5-(1,1-dimethylphenethylaminoacetyl)-8-hydroxycarbostyril (II) was dissolved in 50 ml of methanol, and 1 g of sodium borohydride was added slowly to the solution under ice-water cooling while stirring followed by continuing the stirring at room temperature for an additional hour. The resulting mixture was then adjusted to a pH of 1 with concentrated hydrochloric acid and the mixture was concentrated to dryness. The residue was dissolved in ethanol and any insoluble material was removed by filtration. The ethanolic layer was concentrated to dryness and the residue was dissolved in isopropanol. The isopropanol layer was concentrated and acetone was added to crystallize the product. Recrystallization of the product from methanol-acetone yielded 1.4 g of a white amorphous material having a melting point of 167° – 168° C (with coloring and decomposition). The material thus obtained was confirmed by NMR and IR spectral analyses and elemental analysis to be 5-[2-(1,1-dimethylphenethylamino)-1-hydroxy]ethyl-8-hydroxycarbostyril (I) hydrochloride dihydrate.

EXAMPLE 26

2.5 g of chloranil and 20 ml of xylene were added to 2.2 g of 5-(1-hydroxy-2-amino)ethyl-8-hydroxy-2-amino)3,4-dihydrocarbostyril (VIII), and the mixture was heated under refluxing for 24 hours. The reaction mixture was then concentrated to dryness and the residue was washed thoroughly with carbon tetrachloride. The residue was then dissolved in 30 ml of methanol and the solution was adjusted to a pH of 1 by introducing hydrogen chloride gas into the solution followed by cooling. The precipitated crystals were filtered and recrystallized from methanol to obtain 1.5 g of a material having a melting point of 261° – 262° C (with decomposition). The product thus obtained was confirmed by NMR and IR spectral analyses and elemental analysis as 5-(1-hydroxy-2-amino)-ethyl-8-hydroxycarbostyril (I) hydrochloride.

EXAMPLE 27

200 ml of water, 0.9 g of sodium hydroxide and 4.3 g of Raney nickel were added to 4.3 g of 5-[1-hydroxy-2-(1,1-dimethylphenethylamino]ethyl-8-hydroxy-3,4-dihydrocarbostyril (VIII) hydrochloride dihydrate, and the mixture was heated under refluxing at a temperature of 80° C for 15 hours. The reaction mixture was then filtered to remove the catalyst, and the filtrate was concentrated. The resulting precipitated crystals were recyrstallized from water to obtain 2.6 g of a material having a melting point of 167° – 168° C (with decomposition). The product thus obtained was confirmed by NMR and IR spectral analyses and elemental analysis as 5- 1-hydroxy-2-(1,1-dimethylphenethylamino)]-ethyl-8-hydroxycarbostyril (I) hydrochloride monohydrate.

In the same manner as described in Example 10, the following compound of the formula (I) was prepared:

5-(1-Hydroxy-2-isopropylamino)ethyl-8-hydroxycarbostyril hydrochloride having a melting point of 210°–212° C (with decomposition)

the anesthetic condition constant over the test period. The results obtained are shown in Table I below.

TABLE I

| Compound | Bronchial Resistance (%) Dosage Level (μg/Kg) | | | | | | | | |
|---|---|---|---|---|---|---|---|---|---|
| | 0.01 | 0.03 | 0.1 | 0.3 | 1.0 | 3.0 | 10 | 30 | 100 |
| 5-(1-Hydroxy-2-isopropylamino)ethyl-8-hydroxycarbostyril Hydrochloride | 5.5 | 27.7 | 66.6 | 83.3 | 100 | — | — | — | — |
| 5-(1-Hydroxy-2-tert-butylamino)ethyl-8-hydroxycarbostyril Hydrochloride | 7.3 | 35.5 | 78.6 | 90.4 | 100 | — | — | — | — |
| 5-[1-Hydroxy-2-(α,α-dimethylphenethyl-amino)]ethyl-8-hydroxycarbostyril Hydrochloride | 3.3 | 20.0 | 47.5 | 87.8 | 100 | — | — | — | — |
| (Control) | | | | | | | | | |
| Isoproterenol | 0 | 16.6 | 58.3 | 83.3 | 100 | — | — | — | — |
| Salbutamol | 0 | 0 | 16.6 | 33.3 | 66.6 | 100 | — | — | — |
| Metaproterenol Sulfate (Arotec) | 0 | 0 | 2.7 | 11.1 | 27.5 | 50.0 | 88.3 | 100 | — |
| Quinterenol | 0 | 0 | 0 | 0 | 0 | 0 | 0 | 7.6 | 15.3 |

REFERENCE EXAMPLE

The stimulating activity of the compounds of this invention on β-adreno-receptor was determined as follows:

Male hybrid adult dogs, weighing 10 to 15 Kg were anesthesized with 30 mg/Kg of body weight of sodium pentobarbital administered intravenously. Each of the anesthesized dogs were secured on its back and a cannula was inserted into the trachea. Artificial respiration was conducted using a device according to the Konzett-Rossler method [Konzett H. & Rossler R., "Versuchsanordnug zu Untersuchungen an der Bronchial Moskolatur", Arch. Exp. Path., Pharmack, 195, 71–74, 27–40 (1940)]. The volume of the overflowing air at the time of inhalation was measured through a pneumotachometer to determine bronchial resistance and the values obtained were recorded on a polygraph.

In the above experiment, histamine was employed as a bronchoconstrictor at a dosage level of 10 mg/Kg of body weight, and an aqueous solution containing each of the test compounds and controls shown in Table I below as then administered to each of the anesthesized dogs through the femoral vein at the various dosage levels as shown in Table I below 1 minute before the administration of the histamine. Sodium pentobarbital was infused during the experiment at a dosage level of 4 mg/Kg of body weight/hr. using an automatic injector in order to inhibit spontaneous respiration and to keep Further, the acute toxicity was determined with respect to the test compounds shown in Table II below using 5 to 6 groups each containing 10 male rats (dd strain; body weight, 18 to 22 g) which had been fasted for 12 hours prior to the test. Salbutamol and Isoproterenol were used as a control. The $LD_{50}$ (50% lethal dose) results are as follows.

TABLE II

| Compound | $LD_{50}$ (mg/Kg) | |
|---|---|---|
| | i.v. | p.o. |
| 5-(1-Hydroxy-2-isopropylamino)ethyl-8-hydroxycarbostyril Hydrochloride | 90 (70–115) | 970 (441–2134) |
| 5-[1-Hydroxy-2-(α,α-dimethylphenethyl-amino)]ethyl-8-hydroxycarbostyril Hydrochloride | 102 (84.6–112.8) | 2900 (2180–3560) |
| Salbutamol | 57.1 (52.7–61.9) | 4620* (4160–5130)* 660 (412.5–1056) |
| Isoproterenol | 112.5 (87.9–144.0) | 2587* 355 (235.1–536.1) |

Note: *-Literature values

The compounds of the present invention can be administered at a dosage level of from 100 γ to 50 mg/kg/day by oral, intravenous, intramuscular, intrarectal or inhalation administration in a conventional pharmaceutical dosage form such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The composition may contain other active components which do not adversely affect the activities of the compound of this invention.

Suitable pharmaceutical carriers or diluents include solid carriers such as corn starch, calcium sufate dihydrate, magnesium stearate, lactose, Aerosil (tradename of Nihon Aerosil Co., Ltd. Japan) and the like which are suitable for use in oral, suppository, injectable and inhalant formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using physiologically acceptable carriers or diluents in the form of a solution, suspension or dry preparation which is reconstituted instantaneously with a vehicle for injection just before administration.

The compounds of the present inventio are advantageously administered in the form of an aerosol spray formulation by inhalation.

Typical examples of suitable formulations are given below, but it is to be noted that other dosage forms can also be prepared using other compounds of this invention according to the well-established pharmaceutical techniques.

FORMULATION 1

Tablets each containing the following component were prepared from the following components:

| Components | Amount |
|---|---|
| 5-(1-Hydroxy-2-isopropylamino)ethyl-8-hydroxy-carbostyril | 1 mg |
| Corn Starch | 70 mg |
| Magnesium stearate | 9 mg |
| Lactose | 20 mg |
| Total | 100 mg |

FORMULATION 2

Aerosol spray for inhalation containing the following components per each dose was prepared and filled in the aerosol dispenser:

| Components | Amount |
|---|---|
| 5-(1-Hydroxy-2-isopropylamino)ethyl-8-hydroxycarbostyril | 50 mcg |
| Oleic Acid | 10 mcg |
| Dichlorodifluoromethane | 57 mg |
| Trichlorofluoromethane | 25 mg |

While the invention has been described in detail with reference to specific embodiments thereof, but it is apparent to one skilled in the art that various changes and modifications can be made therein without departing from the spirit and the scope of the present invention.

What is claimed is:

1. A 5-[1-Hydroxy-2-(substituted-amino)]-ethyl-8-hydroxycarbostyril derivative represented by the formula (I)

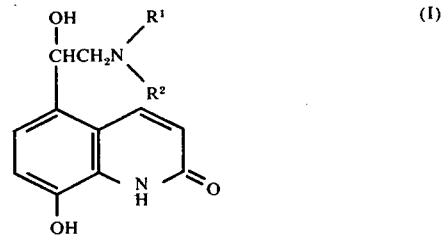

wherein $R^1$ and $R^2$, which may be the same or different, each represents a hydrogen atom or an alkyl group having 1 to 4 carbon atoms, a phenylalkyl group containing a straight or branched chain alkyl moiety having 1 to 4 carbon atoms or a cycloalkyl group having 4 to 6 carbon atoms, or $R^1$ and $R^2$ may, when taken together with the nitrogen atom to which they are attached, form a pyrrolidine, piperidine, morpholine, or piperazine ring which can be unsubstituted or substituted with an alkyl group having 1 to 4 carbon atoms.

2. 5-(1-Hydroxy-2-isopropylamino)ethyl-8-hydroxycarbostyril according to claim 1.

3. 5-(1-Hydroxy-2-sec-butylamino)ethyl-8-hydroxycarbostyril according to claim 1.

4. 5-(1-Hydroxy-2-tert-butylamino)ethyl-8-hydroxycarbostyril according to claim 1.

5. 5-[1-Hydroxy-2-(α-methylbenzylamino)]ethyl-8-hydroxycarbostyril according to claim 1.

6. 5-[1-Hydroxy-2-(α,α-dimethylphenethylamino)]ethyl-8-hydroxycarbostyril according to claim 1.

7. 5-(1-Hydroxy-2-piperidino)ethyl-8-hydroxycarbostyril according to claim 1.

8. 5-(1-Hydroxy-2-morpholino)ethyl-8-hydroxycarbostyril according to claim 1.

9. 5-(1-Hydroxy-2-benzylamino)ethyl-8-hydroxycarbostyril according to claim 1.

10. 5-[1-Hydroxy-2-(1-phenethylamino)]ethyl-8-hydroxycarbostyril according to claim 1.

11. 5-(1-Hydroxy-2-amino)ethyl-8-hydroxycarbostyril according to claim 1.

* * * * *